United States Patent [19]

Koch et al.

[11] Patent Number: 4,943,364
[45] Date of Patent: Jul. 24, 1990

[54] FIBER OPTIC $CO_2$ SENSOR

[75] Inventors: Mark Koch, Mt. Prospect; Richard C. Murray, Jr., Palatine, both of Ill.

[73] Assignee: Spectramed, Inc., Oxnard, Calif.

[21] Appl. No.: 877,572

[22] Filed: Jun. 23, 1986

Related U.S. Application Data

[63] Continuation-in-part of Ser. No. 747,488, Jun. 21, 1985, abandoned.

[51] Int. Cl.⁵ .............................................. G01N 27/26
[52] U.S. Cl. ...................................... 204/415; 204/433
[58] Field of Search ................................ 204/415, 433

[56] References Cited
U.S. PATENT DOCUMENTS 4,194,877 3/1980 Peterson .............................. 526/303

Primary Examiner—Joseph L. Schofer
Assistant Examiner—Bernard Lipman
Attorney, Agent, or Firm—Larry R. Cassett; Roger M. Rathbun

[57] ABSTRACT

A fiber-optic probe for measuring the partial pressure of $CO_2$ in a medium includes a single optical fiber having a distal end; a mirror; a hydrolyzed dye/gel polymer, the dye being in contact with a bicarbonate solution; a solution permeable membrane covering the fiber distal end, hydrogel and mirror; and a gas-permeable membrane covering the solution permeable membrane.

9 Claims, 4 Drawing Sheets

FIG. 1
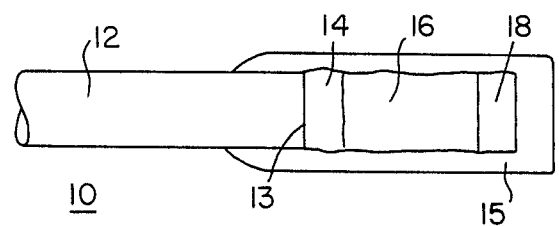
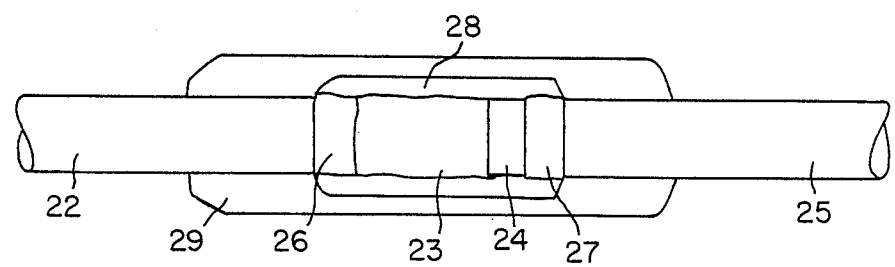
FIG. 2

FIBER OPTIC CO2 SENSOR

BACKGROUND OF THE INVENTION

This invention is a continuation-in-part of U.S. patent application Ser. No. 747,488 filed June 21, 1985, titled "Fiber Optic pH Sensor Having Low Drift Rate", which application is incorporated herein by reference.

This invention relates generally to fiber optic sensors, and more particularly to $CO_2$ sensors. A common method of measuring the partial pressure of carbon dioxide is based on the use of a pH sensor. Typically, the pH sensing material is placed in contact with a solution containing a bicarbonate. The partial pressure of carbon dioxide is determined by fixing the concentration of bicarbonate and then measuring the pH of the solution, which will be proportional to the partial pressure of $CO_2$. The pH-sensing material may be a glass pH electrode or, more simply, a pH-sensing dye.

Fiber optic pH-sensors are based on the principle that certain materials' optical properties change with pH. For example, D. Lubbers et al., "Nanoencapsulated Fluorescence Indicator Molecules Measuring pH and $PO_2$ Down to Submicroscopical Regions on the Basis of the Optode-Principle", *Z. Naturforsch.*, 32c, 133–134, 1977, used a fluorescent material ($\beta$-methyl umbelliferone) encapsulated in polymer beads having porous outer membranes to measure pH. The fluorescent intensity of the material is proportional to pH. Peterson et al., "Fiber Optic Probe for Physiological Use", *Anal. Chem.*, 52, 864–869, 1980, used a colorimetric pH-indicating dye (eg. phenol red) bound to polyacrylamide hydrogel by copolymerization of the dye with the acrylamide monomer in the preparation of their fiber optic pH-sensing probes. The dye changes color with changes in pH, and the color change corresponds to a change in the amount of light of a specified wavelength absorbed by the dye (e.g. green light in the case of phenol red). The Peterson et al. fiber optic probe (also described in U.S. Pat. No. 4,200,110) consists of an ion permeable membrane which encloses the distal ends of a pair of optical fibers. Retained within the hollow membrane and distal to the distal ends of the optical fibers is the pH-indicating sensor (dye/gel polymer). One fiber provides light to the sensing gel and the other fiber transmits the absorbable light from the sensing gel. Thus, the pH of a solution placed in contact with a column of sensing gel, through the ion permeable membrane, can be determined by the intensity of the absorbable light transmitted through the optical fibers.

A problem associated with $pCO_2$ sensors, formed from a pH sensor such as that suggested by Peterson, employing phenol red dye, is leakage of ions across the ion-permeable membrane during the process of achieving equilibrium of the $pCO_2$ between the measuring solution and medium. It has also been difficult to fix the dye/bicarbonate concentrations in the gel used by Peterson. G. G. Vurek proposed a solution to this problem in his U.S. Pat. application Ser. No. 470,920. Vurek's $pCO_2$ sensor includes the same optical arrangement as Peterson, but uses a dye/water/bicarbonate solution contained in a gas-permeable barrier such as silicone rubber. While Vurek's sensor offers advantages in terms of ion impermeability over Peterson's sensor, Vurek's sensor lacks stability with respect to drift and has a slow response time.

pH sensors and pH-based sensors which are used for applications such as continuous patient monitoring are typically manufactured, calibrated, and then sold for use. Once used, the sensors are thrown out. pH sensitive dye/gels change color or fluorescence as a result of changes in the pH of the solution. For analytical purposes it is critical that the color or fluorescent intensity of the dye/gel be constant for a given pH. Sensors made with the conventional dye/gel polymer (such as phenol red/polyacrylamide) show a substantial drift in measured pH with time, resulting from a continual decay in the absorbance of the dye/gel. This drift also corresponds to an increase in the protonation constant, K, of the gel, and severely limits the accuracy of the sensors for pH measurements over extended periods of time (i.e., more than a few hours), or necessitates frequent recalibration of the probes. Furthermore, the initial optimum operating range of these sensors is variable and also drifts with time because of changes in K. All of these factors contribute to a serious lack of reliability in pH-sensors which impedes their use for continuous patient monitoring.

Therefore, it is an object of the present invention to provide a $pCO_2$-sensor having minimal drift and fast response time.

It is another object of the present invention to provide a dye/gel polymer, having a consistently repeatable K value, suitable for use as a $pCO_2$-sensor.

It is yet another object of the present invention to provide a chemically stable $pCO_2$-sensing probe, having minimal drift, suitable to be implanted in tissue for physiological studies.

It is also an object of the present invention to provide an optically stable $pCO_2$-sensing probe, i.e. one in which the color or fluorescence is stable for a given pH and $pCO_2$.

Additional objects, advantages, and novel features of the invention will be set forth in part in the description which follows, and in part will become apparent to those skilled in the art upon examination of the following or may be learned by practice of the invention.

SUMMARY OF THE INVENTION

The invention consists of a special treatment of the dye/gel polymer sensing element which changes its structure sufficiently to render it chemically and optically stable. This sensing element, when in contact with a bicarbonate solution, can then be used in a $pCO_2$ sensor or probe. While not wishing to restrict themselves to any particular theory as to why their treatment solves the aforementioned problems, the inventors believe the cause of the sensor drift was due to the gradual loss of weakly bonded dye molecules from the polymer structure.

The inventors determined that when the initially prepared dye/gel polymer is partially hydrolyzed, the polymer's structure is changed such that substantially all loosely bound dye molecules are removed. The hydrolyzed dye/gel polymer is characterized by chemical and optical stability with respect to dye loss with time. Untreated sensors, when stored in solution release dye and thereby lose calibration. Treated sensors, when stored in solution, release an insignificant amount of dye and retain their calibration with respect to time. Furthermore, the treated dye/gel polymer's effective dissociation constant becomes more consistent from batch to batch and resulting sensors are optically stable with respect to color or fluorescence for a given pH.

A hydrolyzed dye/gel polymer characterized by chemical and optical stability with respect to dye loss with time is preferably prepared by the following technique. The dye/gel polymer is first treated in a dilute base solution for a period of time sufficient to remove the weakly bonded dye molecules from the polymer. The time period depends generally on the temperature at which the process is carried out. Then the dye/gel polymer is washed to remove the base solution and resultant loose dye.

A fiber-optic probe for measuring the partial pressure of carbon dioxide in a medium may comprise a gas-permeable membrane; a hydrolyzed hydrogel within said membrane, the hydrogel being characterized by chemical and optical stability with respect to dye loss with time and the hydrogel including a dye/bicarbonate/gel polymer; means for providing light to the hydrogel; and means for transmitting the absorbable light as a result of changes in $pCO_2$ from the hydrogel. Preferably, a single optical fiber is the light transmitting means and a mirror spaced apart from the fiber end with hydrogel in-between is the transmitting means. Also, a second solution-permeable membrane may be interposed between the hydrogel and gas-permeable membrane.

DESCRIPTION OF THE DRAWINGS

The invention is illustrated in the accompanying drawings wherein:

FIG. 1 is a schematic drawing of an embodiment of the invention having a single membrane.

FIG. 2 is a schematic drawing of another embodiment of the invention having a double membrane.

DESCRIPTION OF THE PREFERRED EMBODIMENT

Figure 3:
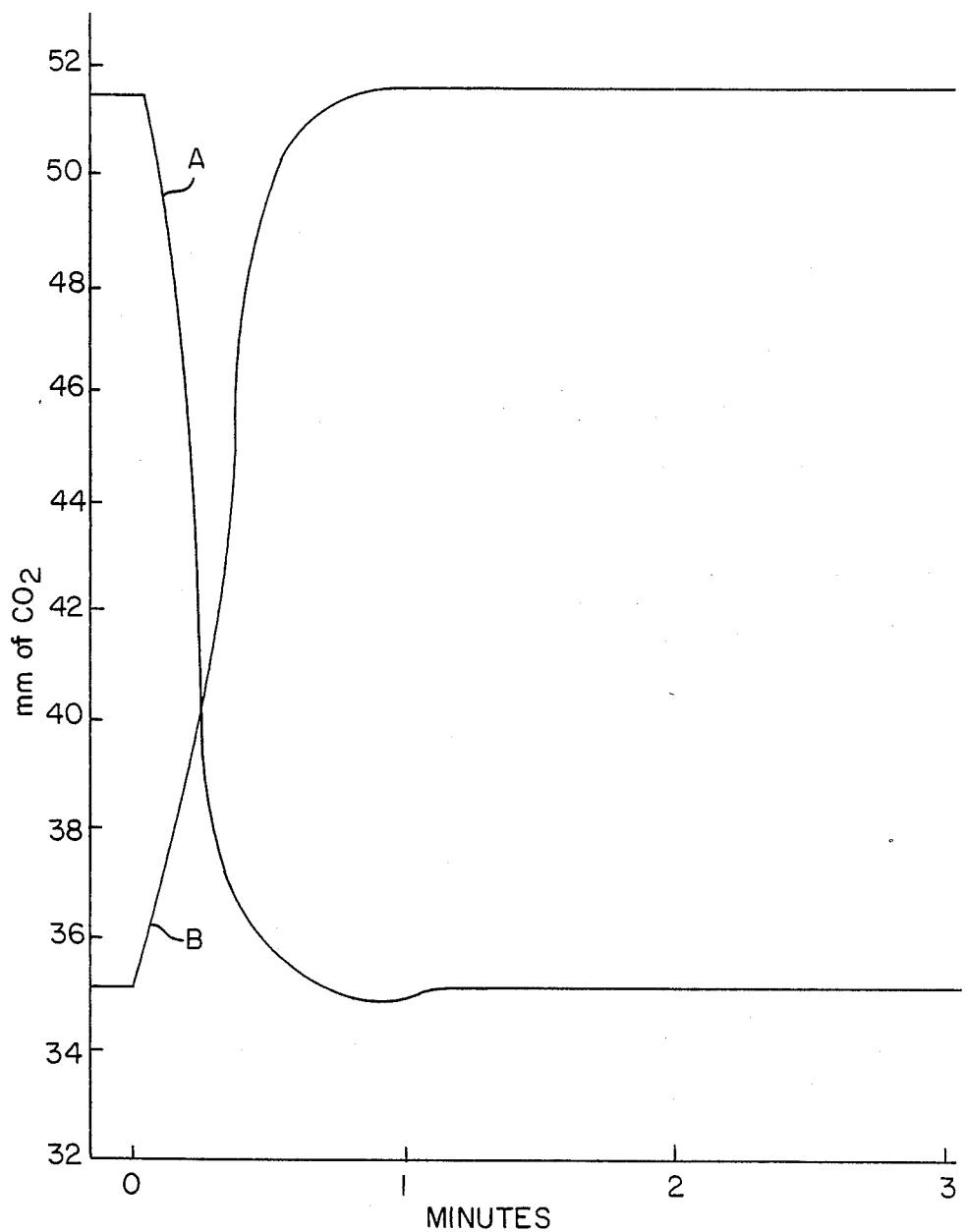
FIG. 3 is a graph of response time in a buffered solution.

While many variations in the following hydrogel treatment will become apparent to those skilled in the art, this particular example produced significant and reproducible results. One gram of synthesized dye/gel polymer, such as polyacrylamide or polyethylene oxide containing phenol red, is added to 100 ml of aqueous 0.025M NaOH in a beaker. Additional dyes which may be used include cresol red, neutral red, and bromothymol blue. The beaker is then covered and placed in a constant temperature oven maintained at 50 degrees C. After a period of about eight hours, the basic solution is decanted off and replaced with 100 ml of distilled water. The container is then returned to the oven. As noted earlier, oven temperature affects the heating time. If the temperature is reduced, the time period should be increased. After about eight to sixteen hours, the dye-containing water is siphoned or decanted off, replaced with fresh distilled water, and returned to the oven. This washing procedure is repeated until the polymer becomes yellow (indicating that all the base has been removed).

The water is then removed from the dye/gel polymer. Several methods are possible. Preferably, the polymer is washed in an anhydrous solvent having a high affinity for water, such as ethanol. This procedure is followed by centrifuging and pouring off the ethanol until the polymer takes on a powdery texture. The ethanol is then decanted off and the gel dried by evaporation.

Variations in the above treatment include: using bases other than NaOH, varying the base concentration, increasing temperature, changing the duration and frequency of the washing cycles. Also, other methods or conditions for producing hydrolysis of weak organic bonds can be used.

The foregoing treatment produces a dye/gel polymer which is chemically and optically stable with respect to dye loss with time, and can be used to produce nearly drift-free pH sensors and pH-based sensors (such as sensors for $CO_2$, $SO_3$ and so on). Such polymers have consistently repeatable K values and are characterized by optical stability with respect to absorbance changes with time.

Referring to FIG. 1, $pCO_2$ sensor 10 includes optical fiber 12 having distal end 13 which is in contact with hydrogel 16 and bound to membrane 15 by adhesive 14. Mirror 18 is positioned opposite distal end 13 with hydrogel 16 in-between. Gas-permeable membrane 15 surrounds distal end 13, hydrogel 16 and mirror 18. Membrane 15 provides a seal around the sensing elements but permits gas to diffuse from the medium to be measured to the hydrogel.

EXAMPLE

Referring to FIG. 2, sensor 20 is fabricated according to the following procedure. Mirror 24 is formed by cutting metal wire into a 2-inch long piece, which is polished to a mirror-like finish. After polishing the mirror is cleaned in a sonic cleaner using acetone for the first wash and alcohol in the second wash and dried thoroughly before use. Next, solution-permeable hollow fiber membrane 28 is formed by cutting, say, hollow dialysis tubing to a length of about 0.5 inch. Additional membranes which may be used include porous polyethylenes, porous polypropylenes and porous Teflon polytetrafluoroethylene. The 2 inch long mirror is then placed into the hollow fiber 28 about 0.05 inch and all but about 0.05 inch of wire is cut from the end of the fiber. This gives mirror 24 a length of about 0.1 inch. In some applications it is necessary to provide an end support for the sensor or probe (see for example co-pending U.S. patent application Ser. No. 779,342 filed Sept. 23, 1985 for "Multiple Sensor Bundle"). For these applications, fiber 25 is provided. A short length of fiber, 25, is fixed to the end of mirror 24 by adhesive (Ablebond 724-8, Ablestik) 27. Then fiber 25 is pushed so that mirror 24 is positioned completely within hollow fiber 28 as well as about 0.1 to 0.2 inch of fiber 25. Excess fiber can be clipped from fiber 25. Adhesive 27 is cured for about twelve hours. Baking at about 55 degrees C can also be done to expedite curing. Next a small portion of hydrogel 23 (dye/gel polymer) is placed within hollow fiber 28. Then a long length (say 4 feet) of optical fiber 22 is placed in the hollow fiber to set the length of hydrogel 23. The end of fiber 22 is then removed and a portion of adhesive 26 is placed between the fiber end and the hydrogel. Adhesive 26 bonds fiber 22 to hollow fiber 28. Adhesive 26 is then allowed to cure for about six hours. The sensor assembly is then placed in a bicarbonate solution of, say, 0.03 M $NaHCO_3$ or 0.03M $NaHCO_3$/0.14M LiCl for about 24 hours in an oven at about 55 degrees C. This conditioning step causes the bicarbonate to come in contact with the dye such that a fixed concentration is achieved. Finally, the sensor is coated with gas-permeable membrane 29. This is accomplished by coating the sensor with a material such as silicone rubber, latex or polyurethane then allowing it to set up.

Figure 4:
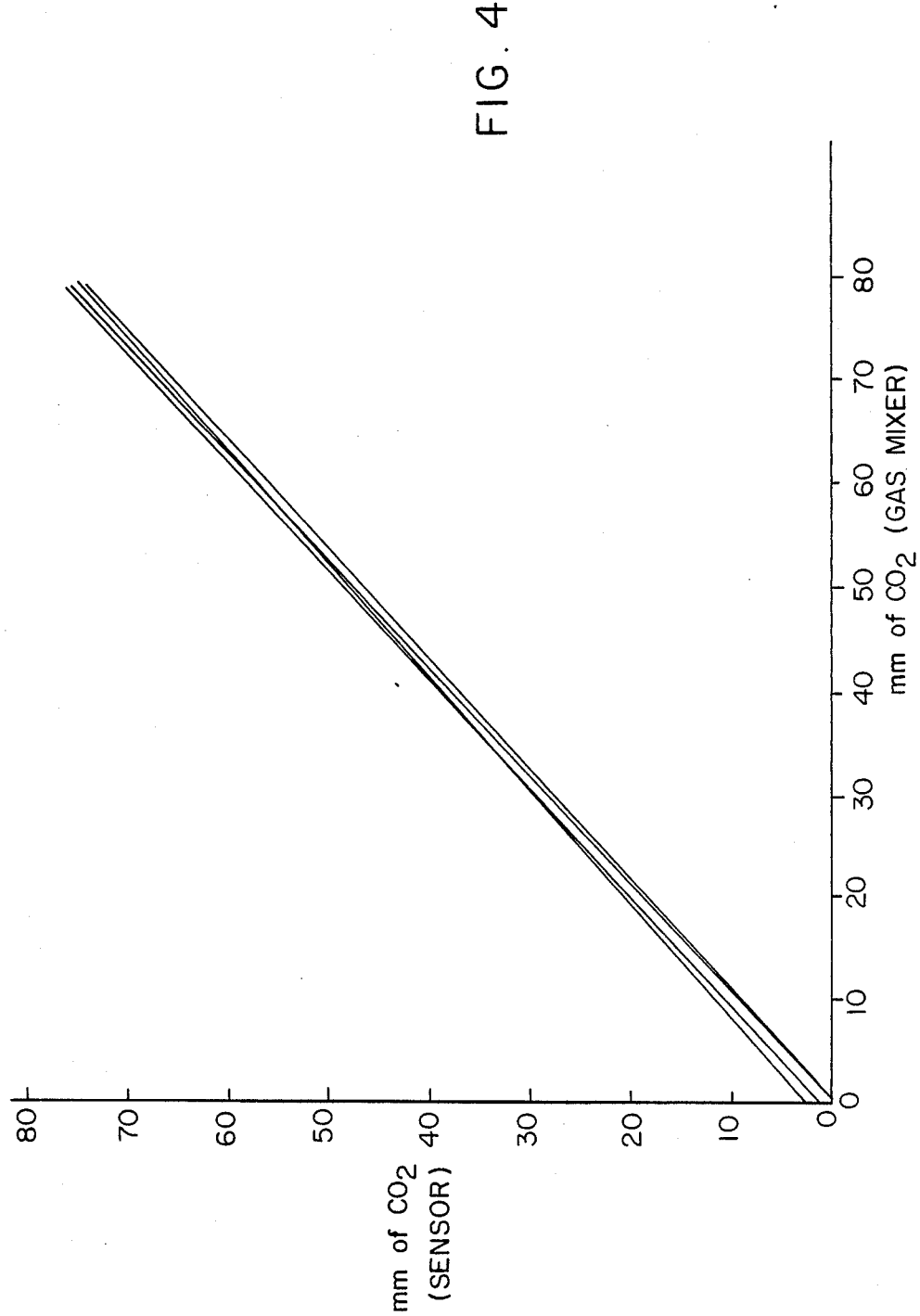
FIG. 4 is a graph of response curves for a sensor over the pressure range 20-80 mm Hg.
Figure 5:
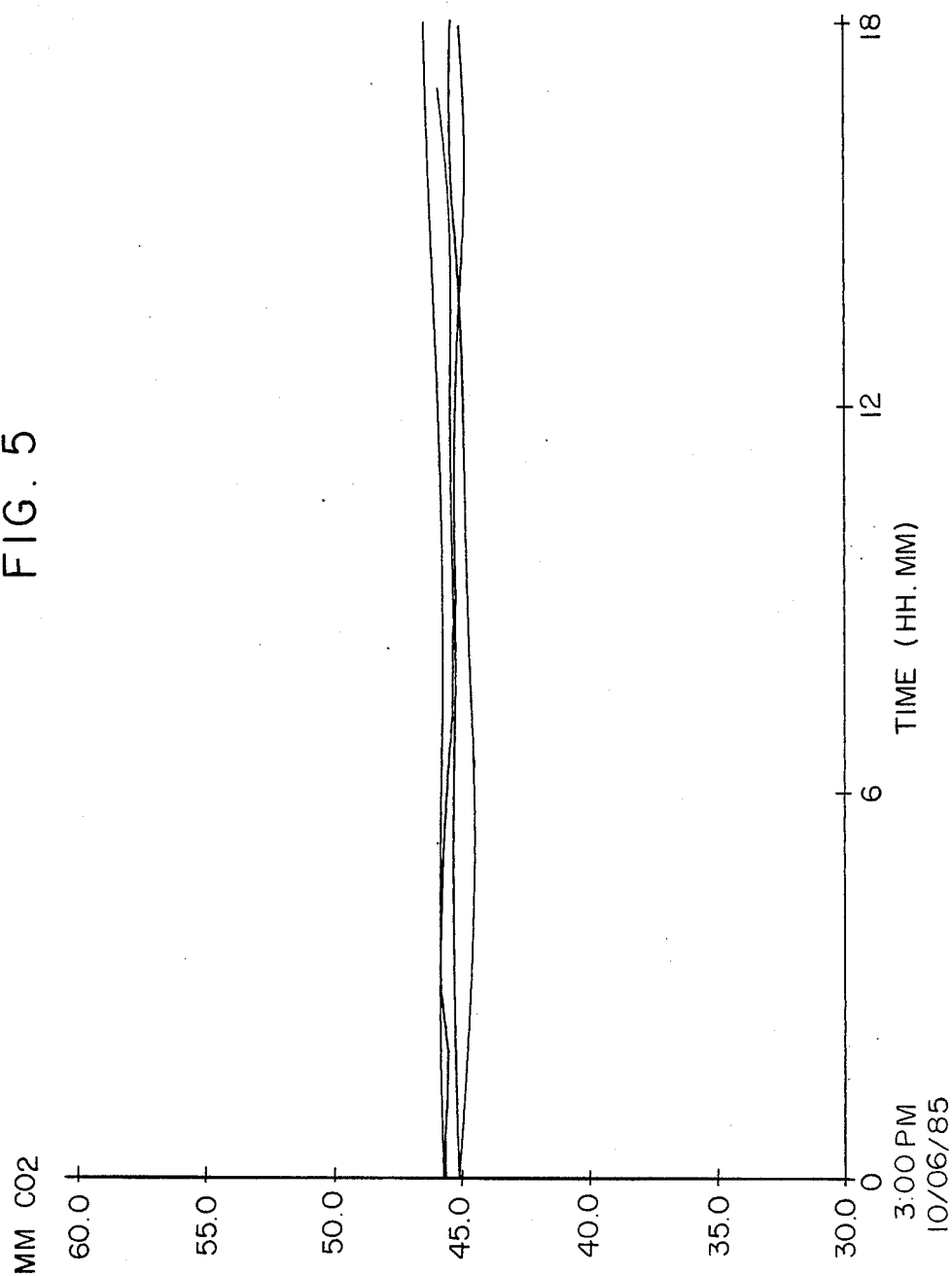
FIG. 5 is a graph of stability over time for a $CO_2$ sensor.

FIG. 3 shows the response characteristic of a $pCO_2$ probe according to the foregoing example. Curves A and B show the response for a 15 mm Hg decrease and increase in response time, respectively. FIG. 4 shows the response curve for a single layer senser over the pressure range of 20–80 mm Hg. FIG. 5 is a graph of drift for four $pCO_2$ probes made according to the example, held at 45.0 mm $CO_2$ for 18 hours.

Although the invention has been described and illustrated in detail, it is to be clearly understood that the same is by way of illustration and example only, and is not to be taken by way of limitation; the spirit and scope of this invention being limited only by the terms of the appended claims.

We claim:

1. A fiber-optic probe for measuring the partial pressure of carbon dioxide in a medium, comprising:

a gas-permeable membrane;

a hydrolyzed hydrogel including a dye/bicarbonate/gel acrylic or ethylene oxide polymer within the gas/permeable membrane, the hydrogel having been prepared from a chemically and optically unstable dye/gel acrylic or ethylene oxide polymer which, prior to treatment, contains weakly bonded dye molecules and exhibits a substantial drift in measured pH with time accompanied by an increase in protonation constant, by a treatment comprising (1) contacting the unstable polymer with a dilute aqueous base solution for a period of time sufficient to remove weakly bonded dye molecules from the polymer (2) washing the base-treated polymer with water to remove substantially all the base, (3) contacting the washed polymer with a solvent having a high affinity for water to remove water from the polymer and give a polymer characterized by chemical and optical stability with respect to dye loss with time and a consistently repeatable protonation constant, and (4) conditioning the stable polymer by contacting it with a bicarbonate solution;

means for providing light to the hydrolyzed hydrogel, and means for transmitting absorbable light from the hydrolyzed hydrogel.

2. A fiber-optic probe as recited in claim 1 wherein the gel polymer is selected from the group consisting of polyacrylamides and polyethylene oxides.

3. A fiber-optic probe as recited in claim 2 wherein the gel polymer is a polyacrylamide.

4. A fiber-optic probe as recited in claim 1 wherein the dye is selected from the group consisting of phenol red, cresol red, neutral red and bromothymol blue.

5. A fiber-optic probe as recited in claim 4 wherein the gel polymer is a polyacrylamide.

6. A fiber-optic probe as recited in claim 1 further comprising a solution-permeable membrane interposed between the gas-permeable membrane and the hydrolyzed hydrogel.

7. A fiber-optic probe as recited in claim 6 wherein the solution-permeable membrane is a hollow fiber membrane selected from the group consisting of porous polyethylenes, porous polypropylenes, porous polytetrafluorethylene and dialysis tubing.

8. A fiber-optic probe as recited in claim 7 wherein the gas-permeable membrane is coated on the exterior of the hollow-fiber membrane and is selected from the group consisting of silicone rubbers, latex rubbers and polyurethanes.

9. A fiber-optic probe as recited in any one of claims 1–8, inclusive, wherein the means for providing light to the hydrolyzed hydrogel comprises an optical fiber having a distal end located within the gas-permeable membrane and the means for transmitting absorbable light from the hydrolyzed hydrogel comprises a mirror located within the gas-permeable membrane, the hydrogel being interposed between the distal end of the optical fiber and the mirror.

* * * * *